(12) United States Patent
Tipler et al.

(10) Patent No.: US 8,404,185 B2
(45) Date of Patent: Mar. 26, 2013

(54) ADSORBENT HOUSING WITH SEPARATED ADSORPTION OUTFLOW AND DESORPTION INFLOW

(75) Inventors: Andrew Tipler, Trumbull, CT (US); Richard G Edwards, Brookfield, CT (US); James E. Botelho, Danbury, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 2241 days.

(21) Appl. No.: 11/407,480

(22) Filed: Apr. 20, 2006

(65) Prior Publication Data

US 2006/0245975 A1    Nov. 2, 2006

Related U.S. Application Data

(63) Continuation of application No. PCT/US2004/035371, filed on Oct. 21, 2004.

(60) Provisional application No. 60/481,549, filed on Oct. 23, 2003.

(51) Int. Cl.
*G01N 30/14* (2006.01)

(52) U.S. Cl. .......... 422/88; 422/89; 73/23.41; 73/23.42; 95/87

(58) Field of Classification Search ............... 422/88, 422/89; 73/23.41, 23.42; 95/87
See application file for complete search history.

(56) References Cited

U.S. PATENT DOCUMENTS

| 3,735,558 | A | | 5/1973 | Skarstrom et al. | .......... 55/16 |
| 4,322,223 | A | | 3/1982 | Christel, Jr. | .......... 55/18 |
| 4,908,676 | A | * | 3/1990 | Bedell et al. | .......... 356/72 |
| 5,932,482 | A | * | 8/1999 | Markelov | .......... 436/181 |
| 6,402,947 | B1 | | 6/2002 | Altamirano et al. | .......... 210/198.2 |

FOREIGN PATENT DOCUMENTS

| WO | WO 94/28409 | 12/1994 |
| WO | WO 03/060508 | 7/2003 |

OTHER PUBLICATIONS

PCT International Search Report, Oct. 6, 2005, 7 pages.

* cited by examiner

*Primary Examiner* — In Suk Bullock
*Assistant Examiner* — Paul Hyun
(74) *Attorney, Agent, or Firm* — St. Onge Steward Johnston & Reens LLC

(57) ABSTRACT

A system for pre-concentrating analytes in a sample prior to introduction into a chromatographic column is generally disclosed comprising a housing, an adsorbent disposed in the housing, and first and second conduits having an inlet and an outlet, respectively, for transferring fluid out of and into the housing during adsorption/dry purge and desorption stages, respectively. In some embodiments, the inlet of the first conduit and the outlet of the second conduit are both disposed in one end of the housing and are offset from each other with respect to the adsorbent.

18 Claims, 8 Drawing Sheets

ADSORBENT HOUSING WITH SEPARATED ADSORPTION OUTFLOW AND DESORPTION INFLOW

PRIOR APPLICATION

The present application is a continuation of International Patent Application No. PCT/US2004/035371, filed Oct. 21, 2004, which designates the United States, and which claims priority benefits under 35 U.S.C. §119(e) of U.S. Provisional Patent Application Ser. No. 60/481,549, filed Oct. 23, 2003.

FIELD OF THE INVENTION

The present invention relates to a system for pre-concentrating analytes in chromatography. More specifically, the invention relates to an analyte pre-concentrator for minimizing the amount of moisture desorbed into a chromatographic column.

BACKGROUND OF THE INVENTION

Gas chromatography is essentially a physical method of separation in which constituents of a test sample in a carrier gas or liquid are adsorbed or absorbed and then desorbed by a stationary phase material into a column. A pulse of the sample is introduced into a steady flow of carrier gas, which carries the sample into the chromatographic column. The inside of the column is lined with a liquid, and interactions between this liquid and the various components of the sample—which differ based upon differences among partition coefficients of the elements—cause the sample to be separated into the respective elements. At the end of the column, the individual components are more or less separated in time. Detection of the gas provides a time-scaled pattern, typically called a chromatogram, that, by calibration or comparison with known samples, indicates the constituents, and the specific concentrations thereof, which are present in the test sample. An example of the process by which this occurs is described in U.S. Pat. No. 5,545,252 to Hinshaw.

Typically, it is desired to pre-concentrate the analytes in the sample, and occasionally, remove moisture therefrom, prior to introducing the sample into the chromatographic column. Accordingly, as disclosed in U.S. Pat. Nos. 5,792,423 and 6,395,560 to Markelov, these systems will typically include some kind of "trap" for this purpose, which retains the analytes as they are carried through the trap, and then later releases these analytes, usually by heating, which are then swept into the chromatographic column.

Various types of traps have been suggested to perform this pre-concentration (and possible moisture removal) prior to introducing the sample into a chromatographic column. One type of trap, and a type that is particularly suited for removing moisture from the sample, is an adsorbent trap, which adsorbs the analytes as the sample is passed through it, which can then later be desorbed. Accordingly, numerous arrangements employing such traps have been employed for the purpose of pre-concentrating the analytes of a sample, which has typically been extracted by some kind of sampling device, such as, for example, a headspace sampler. Examples of such arrangements are disclosed in U.S. Pat. No. 5,932,482 to Markelov and U.S. Pat. No. 6,652,625 to Tipler.

However, to date, these systems have resulted in a number of disadvantages. First, in order to accomplish this multiple stage process of extracting and transferring a sample fluid to the trap, trapping it and untrapping it, and transferring it to the chromatographic column, these systems have employed complex assemblies of parts and/or valves situated in the flow path of the fluid containing the analytes to be measured. These extra devices and valves not only increase cost and space, but increase dead-volume areas and surface active sites. This results in sample dispersion, dilution, or loss, and causes excessive peak broadening on the chromatogram. Another disadvantage present in some of these systems is the unidirectional path of flow for both adsorption and desorption, inhibiting the ability to first trap heavier compounds and then more volatile compounds by using multiple adsorbents.

Accordingly, it has been proposed to use a system incorporating a trap where a carrier gas flows through the trap in one direction as it carries the sample fluid through the trap so that the adsorbent can adsorb the analytes to be measured, and a carrier gas flows through the trap in the opposite direction and carries the analytes out of the trap and to the chromatographic column as the analytes are thermally desorbed from the adsorbent, essentially as described herein. Additionally, it has been proposed to employ a "dry purge" step in between the aforementioned adsorption and desorption steps, where carrier gas flows through the trap in the same direction as it does during the initial adsorption (or "trap load") step in order to purge from the trap any moisture that remained therein, essentially as described herein.

However, even when using these systems, some moisture invariably remains in the trap after the carrier gas has flowed therethrough during the adsorption and dry purge steps. The main reason for this is water condensation. For example, during headspace sampling, when the headspace vapor is transferred from a sample vial, it is saturated with water vapor at a high temperature (e.g., 85 degrees Celsius). During the adsorption (or trap load) step, this sample vapor (including the water vapor) enters the trap, which is maintained at a much lower temperature (e.g., 40 degrees Celsius). Because the saturation concentration of water in the vapor is directly proportional to its vapor pressure, there is immediate condensation of liquid water as the vapor pressure is reduced upon entry into the trap.

Similarly, the outlet tubing through which fluid is discharged from the trap after it has passed through the adsorbent is often at a lower temperature than the trap. Accordingly, condensation of water vapor will also take place in the outlet tubing. Therefore, even when a dry purge step is employed to try to sweep out residual water that remained in the trap after the adsorption (trap load) step, the dry purge step itself will result in some residual water.

Due to this condensation, one of the very objects that the trap seeks to achieve—namely, the elimination of unwanted moisture—is not fully accomplished. This is because the aforementioned outlet tubing also acts as an inlet for fluid during the desorption stage, serving as a supply line for carrier gas, which flows back through the trap to pick up the previously adsorbed analytes and sweep them back out of the trap and into the chromatographic column as the analytes are desorbed from the adsorbent. Because this carrier gas is flowing back over the areas where the water condensed, it sweeps this water back out of the tubing and the trap and into the chromatographic column along with the desorbed analytes.

What is desired, therefore, is a system for pre-concentrating analytes in a sample prior to introduction into a chromatographic column that is inexpensive to manufacture, does not take up a lot of space, and reduces the amount of dead volume areas and surface active sites. What is further desired is a system for pre-concentrating analytes in a sample prior to introduction into a chromatographic column that does not sweep into the chromatographic column water that has condensed during the adsorption and/or dry purge phases of the process. What is also desired is a system for pre-concentrating analytes in a sample prior to introduction into a chromatographic column that does not require substantial temperature control of multiple parts of the system.

SUMMARY OF THE INVENTION

Accordingly, an object of the present invention is to provide a system for pre-concentrating analytes in a sample prior to introduction into a chromatographic column that minimizes the use of extra devices to trap and transfer the analytes in the sample to be measured.

It is a further object of the present invention to provide a system for pre-concentrating analytes in a sample prior to introduction into a chromatographic column that eliminates the use of valves in the flow path of the analytes to be measured.

It is another object of the present invention to provide a system for pre-concentrating analytes in a sample prior to introduction into a chromatographic column that minimizes the number of parts of the system that must be heated.

It is yet another object of the present invention to provide a system for pre-concentrating analytes in a sample prior to introduction into a chromatographic column that adsorbs analytes as fluid carrying the analytes flows in one direction and desorbs the analytes as fluid flows in the opposite direction.

It is still another object of the present invention to provide a system for pre-concentrating analytes in a sample prior to introduction into a chromatographic column that prevents water that has condensed in the outlet tubing for the adsorbent and/or dry purge stages from being swept into the chromatographic column as fluid carries desorbed analytes into the column.

It is yet another object of the present invention to provide a system for pre-concentrating analytes in a sample prior to introduction into a chromatographic column that prevents water that has condensed in the trap from being swept into the chromatographic column as fluid carries desorbed analytes into the column.

To overcome the deficiencies of the prior art and to achieve at least some of the objects and advantages listed, the invention comprises an analyte pre-concentrator for pre-concentrating analytes in a sample, including an adsorbent housing having a first end for receiving the sample containing the analytes and a second end, an adsorbent disposed in the housing for adsorbing the analytes, a first conduit in fluid communication with the second end of the housing for venting fluid that has passed through the adsorbent, and a second conduit in fluid communication with the second end of the housing for supplying fluid to the housing during desorption of the analytes from the adsorbent, wherein the first conduit has a conduit inlet for receiving fluid from the housing, the second conduit has a conduit outlet for discharging fluid into the housing, and the conduit inlet of the first conduit is different from the conduit outlet of the second conduit.

DETAILED DESCRIPTION OF THE INVENTION

Figure 1:
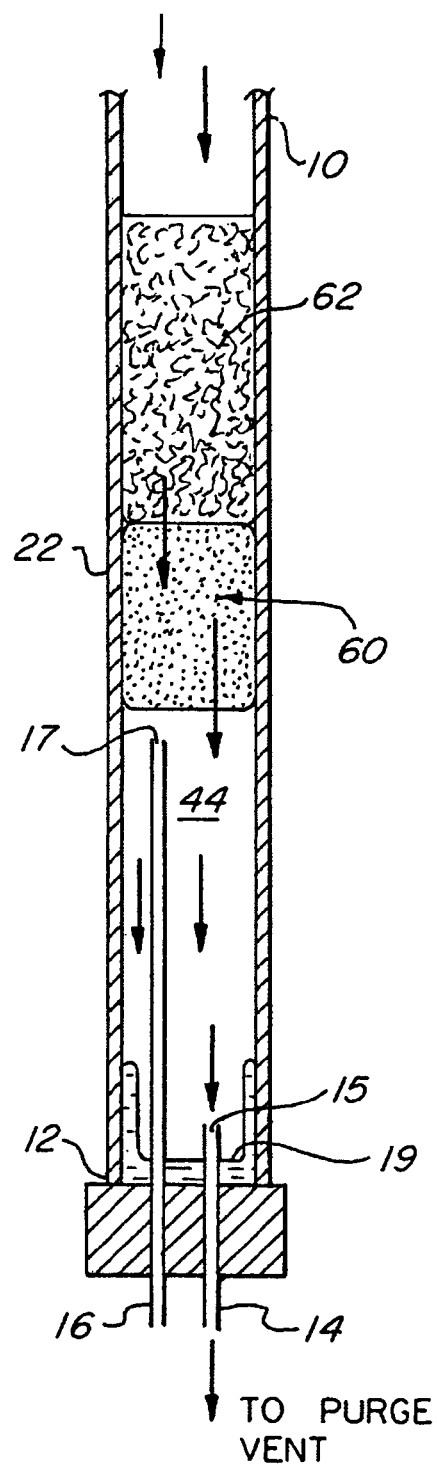
FIG. 1 is a schematic view of an analyte pre-concentrator in accordance with invention during the dry purge stage.

The basic components of one embodiment of an analyte pre-concentrator in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

An adsorbent housing 22 includes a first end 10 for receiving a sample in any of a variety of ways, an example of which is further described below. The housing, which is typically a tube or liner of some sort, also has a second end 12, as well as a flow channel 44 therein. At least one adsorbent 60 is disposed in the flow channel 44 in order to adsorb the analytes in the sample as the sample fluid passes through the first end 10 and down into the flow channel 44. In certain advantageous embodiments, a weaker adsorbent 62 is positioned between the first end 10 and the adsorbent 60. Accordingly, as the sample fluid passes through the first end 10 and down into the flow channel 44, the weaker adsorbent 62 first adsorbs the heavier compounds, and the stronger adsorbent 60 then adsorbs the more volatile compounds in the sample.

In some embodiments, the adsorbents 60, 62 are hydrophobic, thereby allowing moisture to be easily purged from the system by a carrier gas, as further explained below. However, in other embodiments, when the measurement of very volatile VOCs (such as vinyl chloride, Freons, and gaseous hydrocarbons) is desired, a very strong adsorbent is required, and thus, adsorbent 60 may be somewhat hydrophilic. In certain advantageous embodiments, graphitized carbon black is used as an adsorbent. In some embodiments, a polymeric adsorbent is used. In certain embodiments, a carbon molecular sieve is used.

A first conduit 14 is in fluid communication with the flow channel 44 in order to transfer fluid that has passed through the adsorbents 60, 62 out of the housing 22. The conduit 14 has an inlet 15 for receiving the fluid from the housing 22 and, in certain advantageous embodiments, is disposed in the second end 12 of the housing 22. A separate, second conduit 16 is also in fluid communication with the flow channel 44 for transferring carrier gas into the housing when such fluid is required in order to carry analytes previously adsorbed by the adsorbents 60, 62 out of the housing 22. The conduit 16 has an outlet 17 for introducing the carrier gas into the housing 22 and, in certain advantageous embodiments, is also disposed in the second end 12 of the housing 22.

In certain advantageous embodiments, the inlet 15 of the first conduit, which vents fluid during the adsorption and/or dry purge, is offset from the outlet 17 of the second conduit 16, which supplies carrier gas during desorption. Accordingly, the distance between the outlet 17 and the adsorbent 60 may be less than the distance between the inlet 15 and the adsorbent 60.

In some embodiments, the adsorbent housing 22 includes a heating element so that it is temperature controllable. Accordingly, the housing 22 can be heated to desorb analytes that have been previously retained by the adsorbents 60, 62 before a fluid sweeps them out of the housing 22, as is further described below.

The basic components of one example of a chromatographic system employing the analyte pre-concentrator described above are illustrated in FIG. 3. This system includes an interface housing 20, and the adsorbent housing 22 is connected thereto. In some systems, the interface housing 20 and the adsorbent housing 22 have corresponding threaded portions so that the adsorbent housing 22 can be easily connected to and removed from the system. However, in other systems, the adsorbent housing 22 may be connected to the interface housing 20 via any other means providing an adequate seal such that fluid leakage does not occur, and in some cases, the adsorbent housing 22 is even integrally formed with the interface housing 20.

The interface housing 20 has a first end 24 and a second end 26. The first end 24 is adapted to be coupled to sampling device, such as, for example, a headspace sampler. The second end 26 is adapted to be coupled to a chromatograph. This may be accomplished, for example, by the use of a column port 28 in the interface housing 20 for receiving the end of a chromatographic column 50.

The sampling device to which the first end 24 of the interface housing 20 is coupled will typically include some vessel or area for holding and/or extracting a sample containing analytes to be measured. For example, the sampling device may include a sampling needle 30 and a sample chamber 32, where the sampling needle has a vessel port 34 through which fluid is communicated between the needle 30 and a vessel 38 and a sample chamber port 36 through which fluid is communicated between the needle 30 the sample chamber 32.

The interface housing 20 has a flow channel 40 therein, and a first valveless conduit 42 permits fluid to be communicated between the sample chamber 32 and flow channel 40. Similarly, a second valveless conduit 46 permits fluid to be communicated between the flow channel 40 and the flow channel 44.

As noted above, in some systems, the interface housing 20 has a column port 28 for receiving the end of a chromatographic column 50. A third valveless conduit 48 permits fluid to be communicated between the first flow channel 40 and the column 50. The third valveless conduit 48 may comprise a channel of the column port 28 that is in fluid communication with the flow channel 40 and is especially adapted for receiving the end of the column 50, or it may comprise a portion of the flow channel 40 adjacent to the end of the column 50, or it may simply be the end of the column 50 itself.

The interface housing 20 has a first inlet 72 for generally providing needed fluid to the system. For instance, the first inlet 72 may provide carrier gas to different parts of the system at different stages of operation, such as, for example, by providing the sampling device with fluid to pressurize the vessel 38, or, as another example, by providing carrier gas to the adsorbent housing 22 to carry a sample containing analytes thereto or to sweep away moisture contained therein. The interface housing 20 also has a second inlet 74 for providing fluid that may be used by various parts of the system at various stages, but primarily for isolating the chromatographic column 50 from the rest of the system in order to keep fluid from entering the column 50 until it is specifically desired to desorb the analytes thereinto. Valves 76, 78 are provided to open and close inlets 72, 74, respectively.

It should be noted that, while the adsorbent housing 22 has been described herein in connection with the interface assembly 20, various other arrangements may be used for coupling the adsorbent housing 22 to the sampling device and the column 50, such as, for example, chromatographic injectors, various types of transfer lines, and various column isolating accessories.

Figure 3:
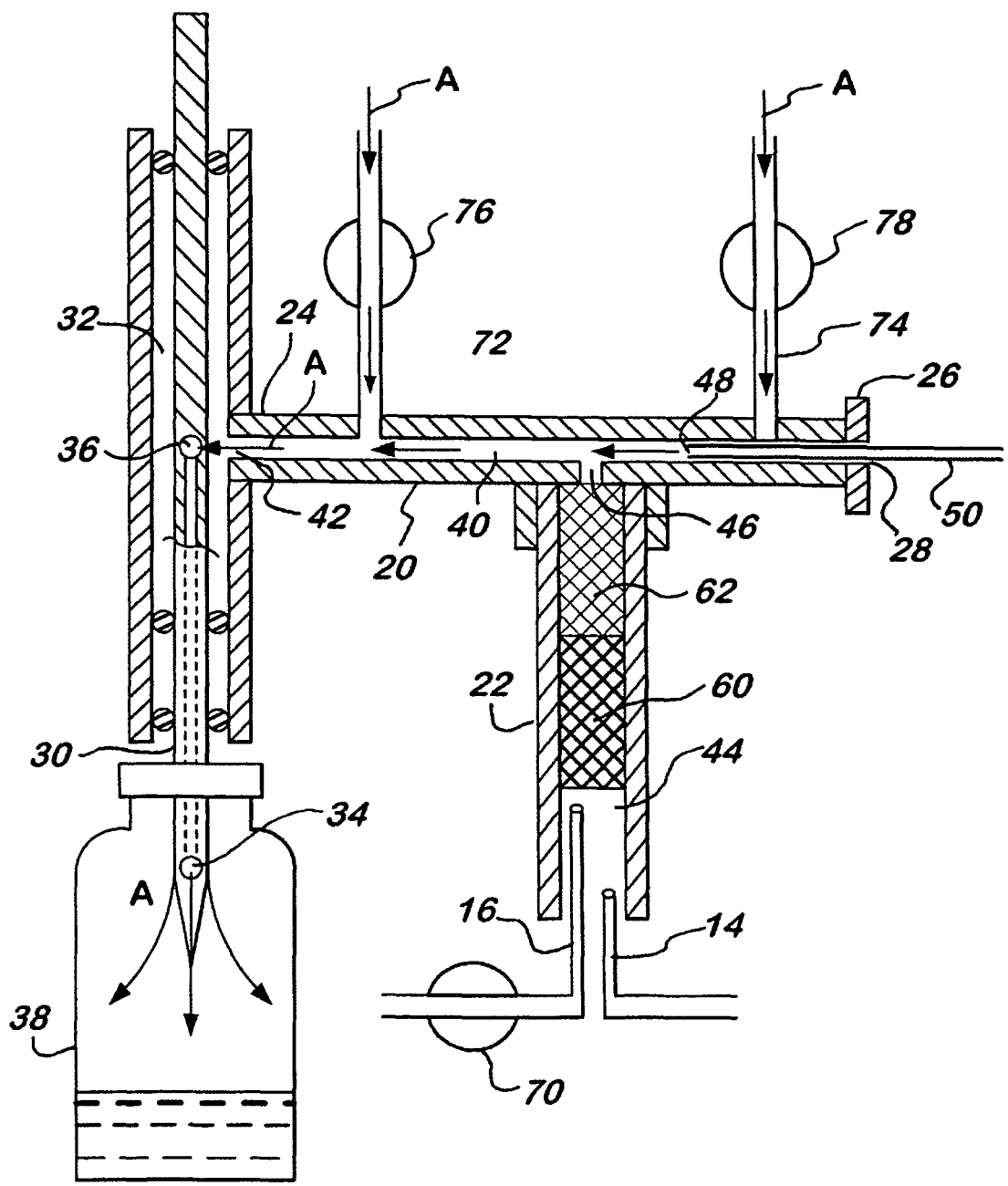
FIG. 3 is a schematic view of a system using the analyte pre-concentrator of FIGS. 1-2 during a vial pressurization stage.

Operation of the above described assembly is illustrated stepwise in FIGS. 3-6. A pressurization step is illustrated in FIG. 3. As shown therein, the sampling needle 30 descends into the vessel 38, bringing the vessel port 34 into fluid communication with the interior of the vessel 38. The valves 70, 76, 78, are all open, sending fluid into the sample chamber 32, through the chamber port 36, down through the needle 30, and into the vessel 38 (indicated by arrows A). In this way, the vessel is pressurized.

Figure 4:
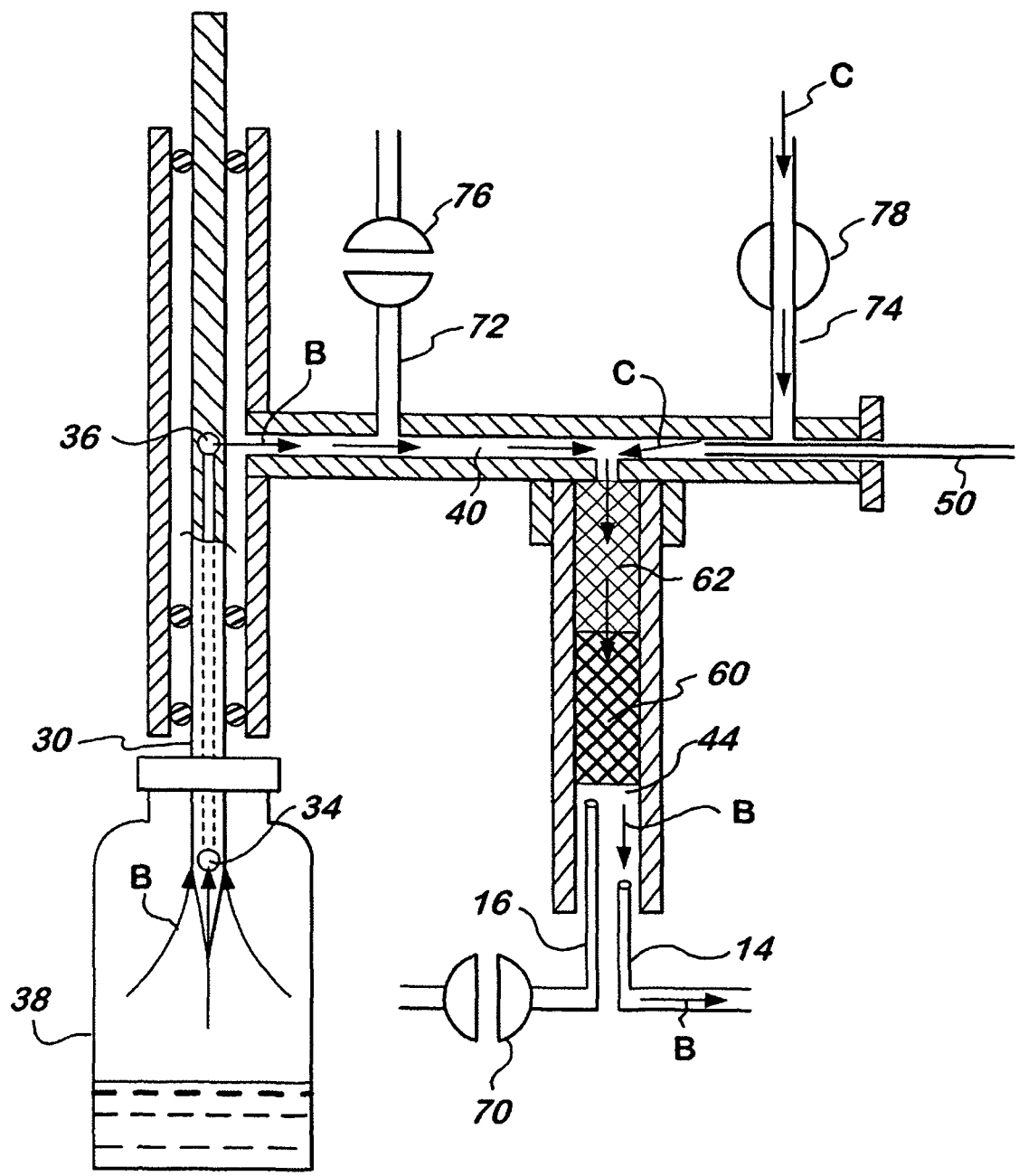
FIG. 4 is a schematic view of the system of FIG. 3 during an adsorption, or trap load, stage.

An adsorption, or trap load, step is illustrated in FIG. 4. As shown therein, the inlet valve 76 is closed, terminating the supply of fluid from the inlet 72. Likewise, a valve 70 terminates the supply of fluid from the conduit 16. As a result, fluid containing the analytes to be measured elute from the vessel 38 through the vessel port 34, through the needle 30, out the chamber port 36, into the flow channel 40, into the flow channel 44 and through the adsorbents 62, 60, which adsorb the analytes before the fluid is discharged through the conduit 14 (indicated by arrows B). The inlet valve 78 remains open, allowing fluid to continue to enter through the inlet 74 and isolate the column 50 (indicated by arrows C). As can be seen in FIG. 1, moisture (indicated at 19) condenses at the second end 12 of the housing 22, past the outlet 17 of the conduit 16, which, as further described below, will supply carrier gas to the housing 22 during the desorption step for sweeping analytes out of the housing 22.

Figure 5:
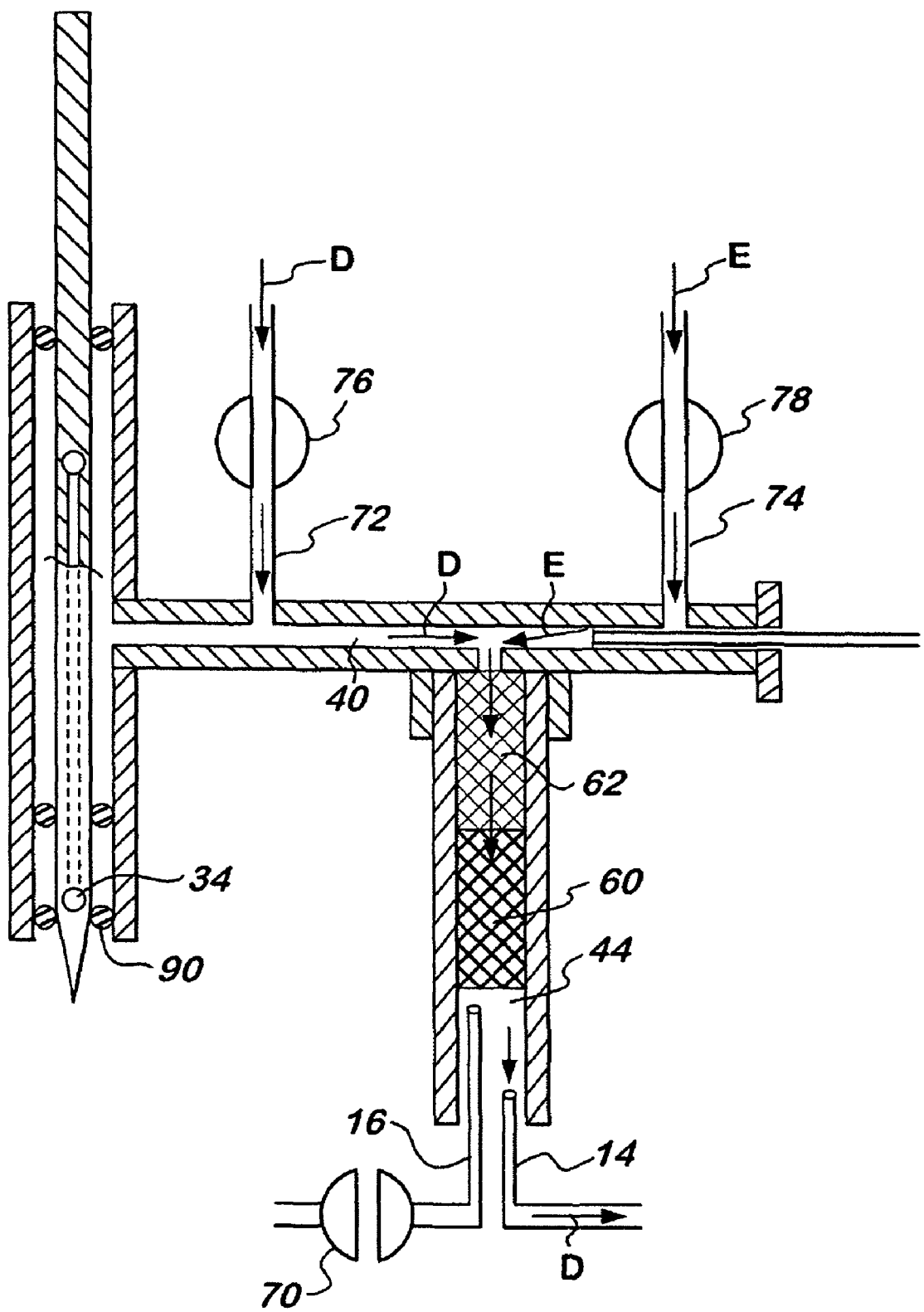
FIG. 5 is a schematic view of the system of FIG. 3 during a dry purge stage.

In embodiments where a significant amount of moisture is present in the sample being analyzed, a dry purge step may be desired, which is illustrated in FIG. 5. As shown, the needle 30 is withdrawn from the vessel 38, bringing the vessel port 34 above the seal 90. The inlet valve 76 is opened again, thereby allowing fluid to once again enter the system via the inlet 72. The fluid flows into the flow channel 40, into the flow channel 44 and through the adsorbents 62, 60, sweeping any moisture therein out through the conduit 14 (indicated by arrows D). Once again, the inlet valve 78 remains open, allowing fluid to continue to enter through the inlet 74 and isolate the column 50 (indicated by arrows E).

Figure 2:
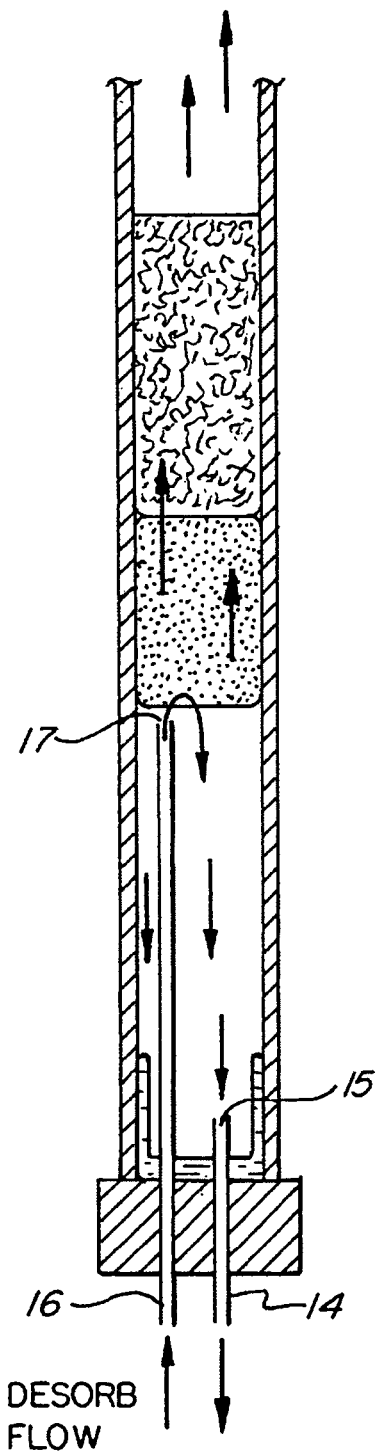
FIG. 2 is a schematic view of the analyte pre-concentrator of FIG. 1 during the desorption stage.
Figure 6:
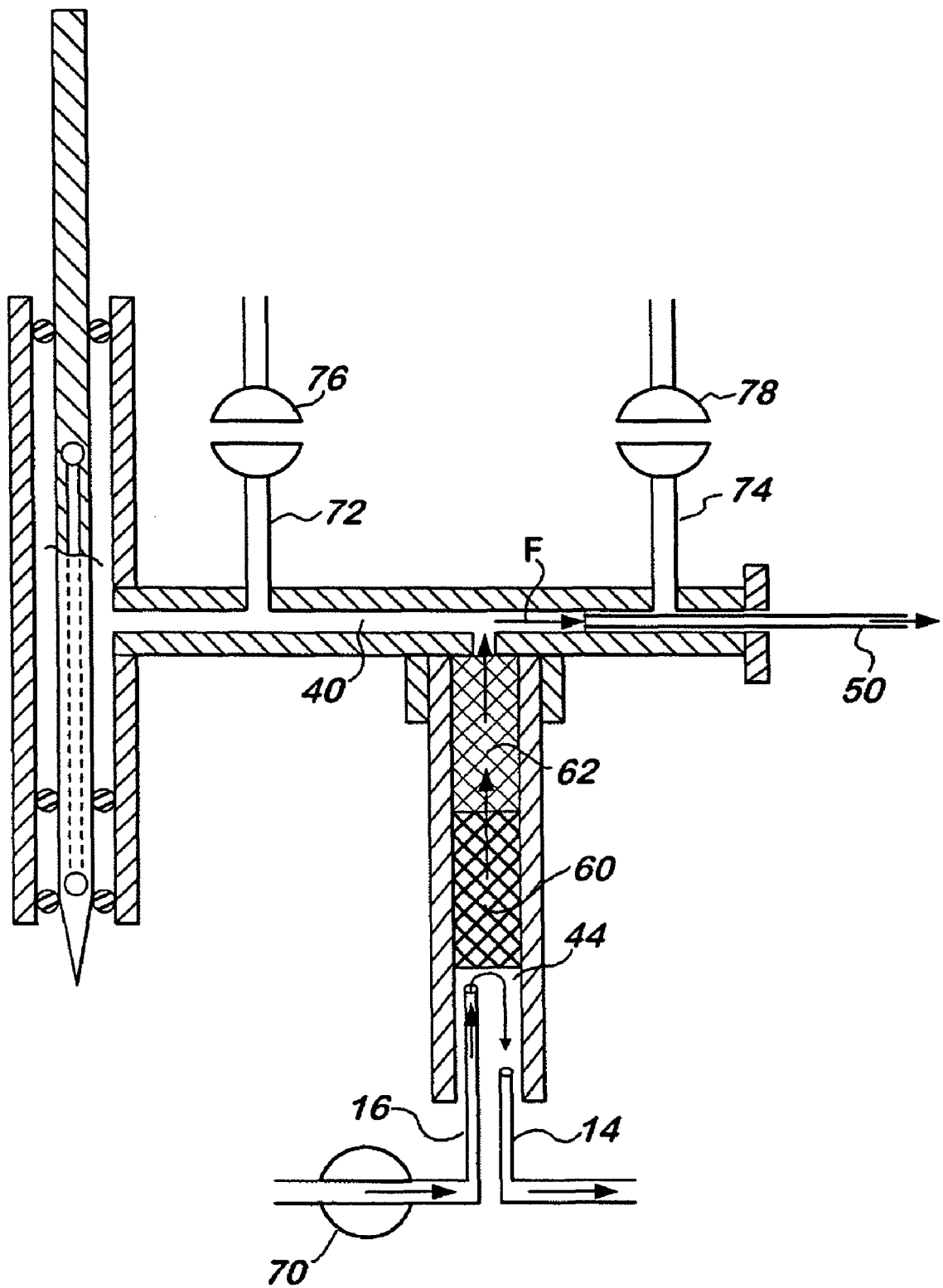
FIG. 6 is a schematic view of the system of FIG. 3 during a desorption stage.

A desorption step is illustrated in FIG. 6. As shown therein, the valves 76, 78 are closed, terminating the supply of fluid from inlets 72, 74. The valve 70 is open, thereby introducing fluid into the housing 22. The adsorbent housing 22 is heated to desorb the analytes retained by the adsorbents 62, 60. Fluid enters through the conduit 16, flows into the flow chamber 44, sweeping the desorbed analytes into the flow chamber 40 and into the chromatographic column 50 (indicated by arrows F). As can be seen in FIG. 2, the fluid enters the housing 22 from the outlet 17, which is past the moisture that has condensed at the bottom of the housing 22. Because the carrier gas supplied for the desorption step does not flow through either the conduit 14 or the bottom of the housing 22, it does not sweep any of the moisture that has condensed in those locations back through the housing 22 towards the chromatographic column 50. Additionally, some of the carrier gas entering the housing 22 via the outlet 17 also flows downwards towards the inlet 15 of the conduit 14, continuing to force condensed water out through the conduit 16 and helping to ensure that none of this condensed water flows back towards the adsorbent 60.

Figure 7:
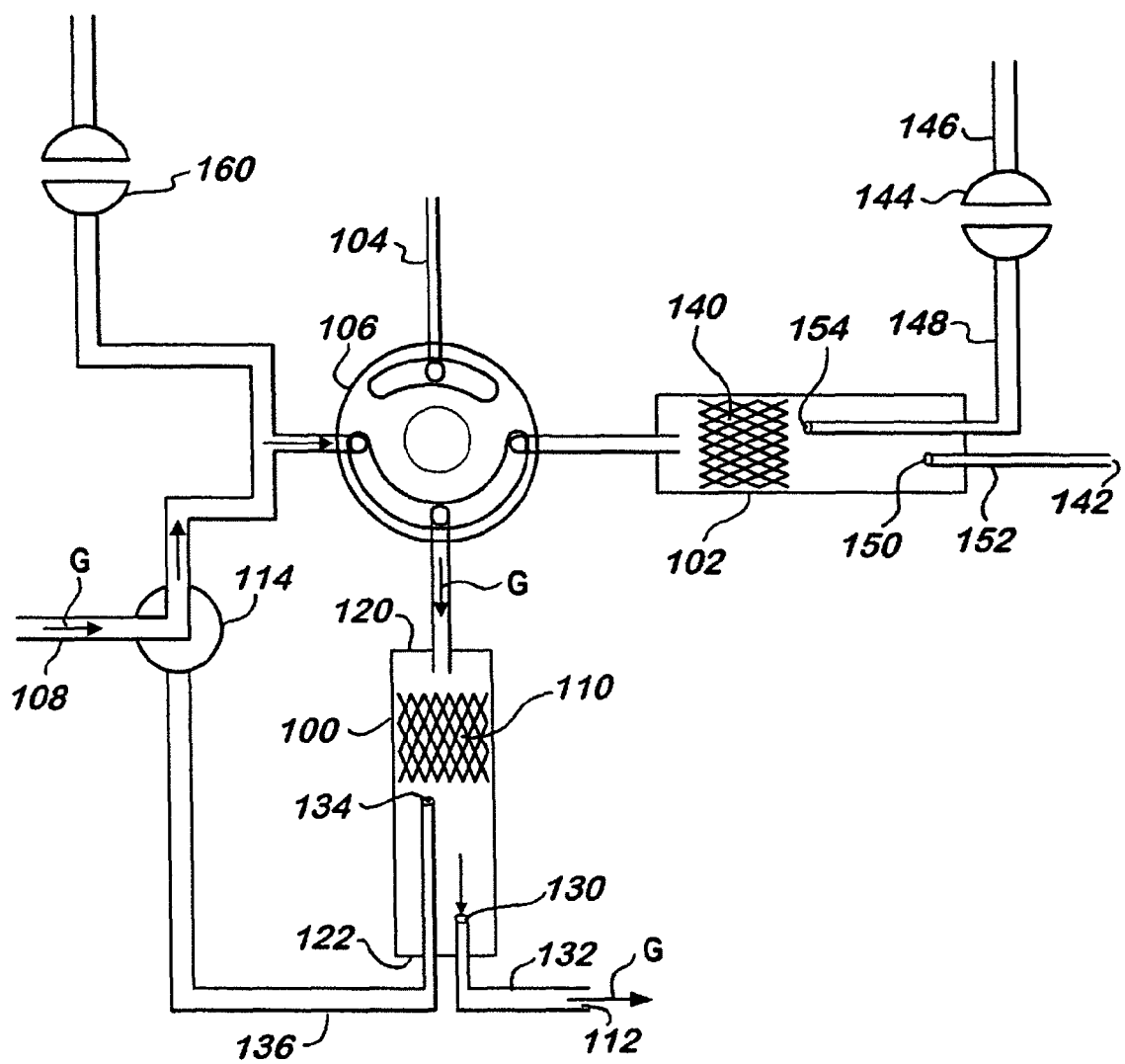
FIG. 7 is a schematic view of a system using the analyte pre-concentrator of FIGS. 1-2 during a sample vessel dry purge stage.

In certain systems, instead of using a auto-sampling device, such as the headspace sampler discussed above, a vessel, such as the sorbent tube 100 shown in FIG. 7, is transported to a location from which a sample is to be collected. Depending on the particular application, the sample may be collected in the vessel 100 in different ways, such as, for example, by pumping the sample into the vessel 100, or, in a particular environment to be tested, by allowing components in the air to simply migrate into the vessel 100 through natural diffusion. The vessel 100 is then transported to a thermal desorption device, where it may be placed in fluid communication with a separate adsorbent trap 102 for further concentration of the analytes prior to desorption into the chromatographic column 104, as shown in FIG. 7.

Figure 8:
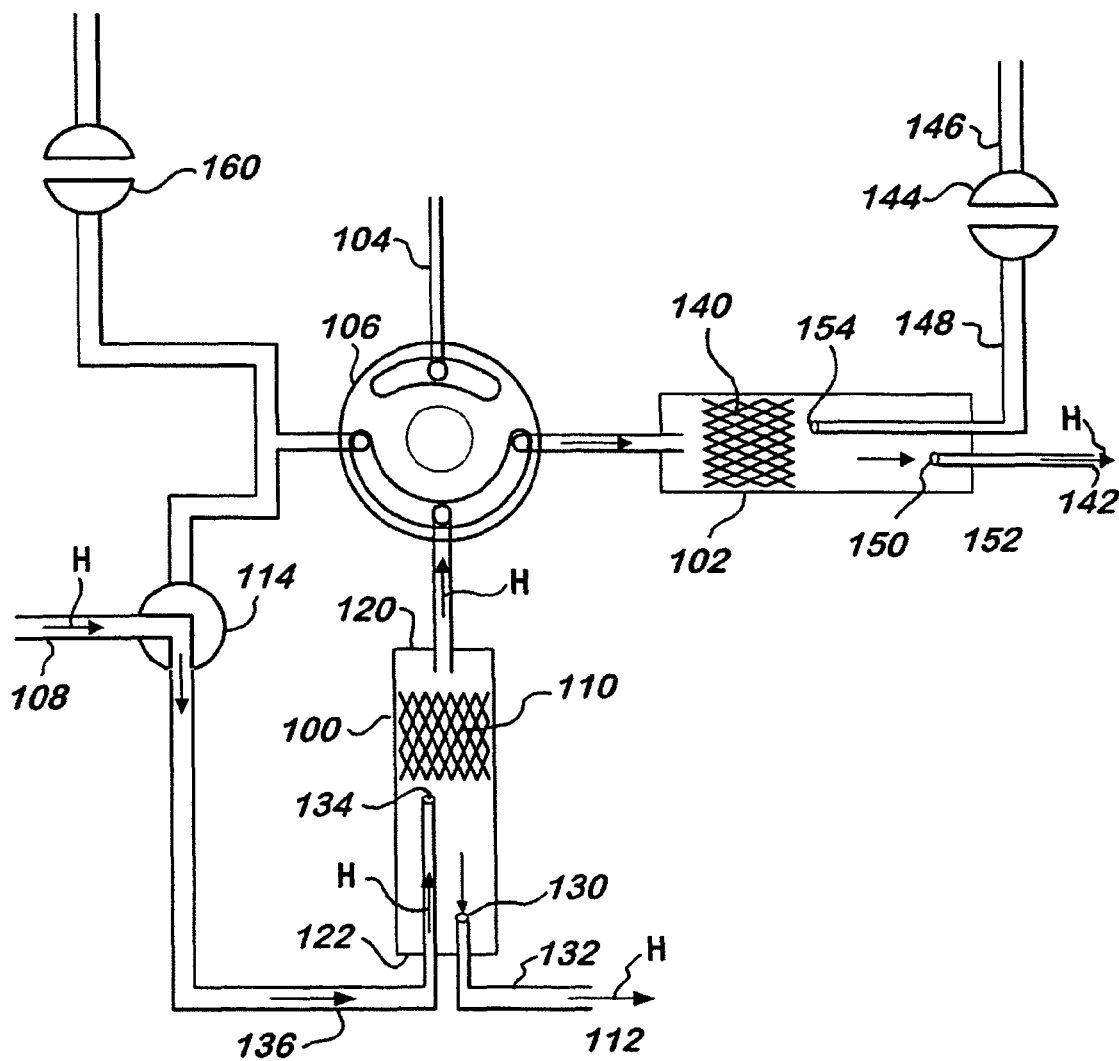
FIG. 8 is a schematic view of the system of FIG. 7 during a sample vessel desorption and trap load/purge stage.
Figure 9:
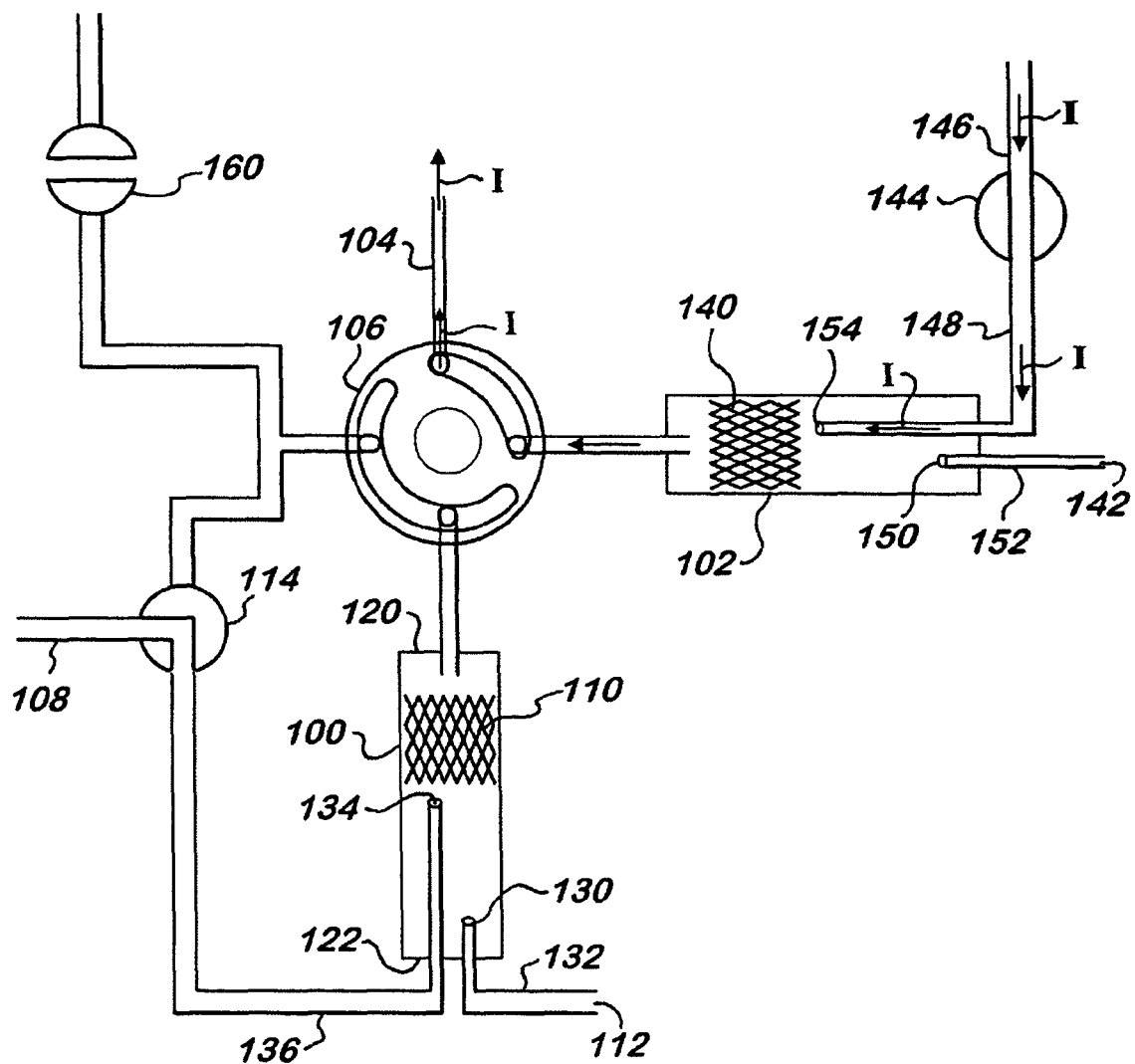
FIG. 9 is a schematic view of the system of FIG. 7 during a trap desorption stage.

Operation of such a system is illustrated stepwise in FIGS. 7-9. A sample vessel dry purge step is illustrated in FIG. 7. As shown therein, a rotary valve 106 is positioned such that a carrier gas inlet 108, the sample vessel 100, and the trap 102 are in fluid communication. Carrier gas flows from the inlet 108 to the first end 120 of the sample vessel 100. The gas enters the vessel 100 through the first end 120, flows through the adsorbent 110, flows out of the vessel 100 via the inlet 130 of conduit 132, and exits through the vent 112, indicated by arrows G. In this way, moisture in the vessel 100 is purged therefrom. In certain embodiments, a valve 160 is also provided in the event a split flow is desired.

A sample vessel desorption and trap load/purge step is illustrated in FIG. 8. As shown therein, a diverter valve 114 directs carrier gas from the inlet 108 to the second end 122 of the sample vessel 100. The carrier gas flows into the vessel 100 via the outlet 134 of the conduit 136, through the adsorbent 110, out through the first end 120 of the vessel 100, and into the trap 102, indicated by arrows H. In this way, the carrier gas, sweeps up the analytes as they are desorbed from the adsorbent 110 and carries them into the trap 102. The adsorbent 140 in the trap 102 adsorbs the analytes, and the carrier gas flows out of the trap 102 via the inlet 150 of the conduit 152 and exits through the vent 142, also indicated by arrows H.

A trap desorption step is illustrated in FIG. 9. As shown therein, the rotary valve 106 is rotated and the valve 144 is opened. Carrier gas flows from the inlet 146, through the conduit 148, and into the trap 102 via the outlet 154. The gas then flows through the adsorbent 140, sweeping up the analytes as they are desorbed, and carrying them out of the trap 102 and into the chromatographic column 104, indicated by arrows I.

As in the case of the headspace applications previously described, the adsorbent housings 100, 102 each have separated outflow and inflow conduits for dry purging and desorption, respectively. As shown in FIGS. 7-9, the conduit outlet 134 of conduit 136 is offset from the conduit inlet 130 of conduit 132 and is located closer to the adsorbent 110. Accordingly, any moisture that remains in the second end 122 of the sample vessel 100 after the dry purge step (i.e., when the carrier gas exits through the conduit inlet 130) does not get swept back through the adsorbent 110 when carrier gas enters the vessel 100 via the conduit outlet 134 during the desorption step. Similarly, the conduit outlet 154 of conduit 148 is offset from the conduit inlet 150 of conduit 152 and is closer to the adsorbent 140. Accordingly, any moisture that remains in the trap 102 after the trap is dry purged does not get swept back through the adsorbent 140 when carrier gas enters the trap 102 via the conduit outlet 154 during desorption.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. An analyte pre-concentrator for pre-concentrating analytes in a sample, comprising:
    an adsorbent housing having a first end for receiving the sample containing the analytes and a second end;
    an adsorbent disposed in said housing for adsorbing the analytes;
    a first conduit in fluid communication with the second end of said housing for venting fluid that has passed through said adsorbent; and
    a second conduit in fluid communication with the second end of said housing for supplying fluid to said housing during desorption of the analytes from said adsorbent;
    wherein said second conduit includes a conduit outlet from which fluid enters said housing, said first conduit has a conduit inlet for receiving fluid from said housing, the conduit inlet of said first conduit is different from the conduit outlet of said second conduit, and the distance between the conduit outlet of said second conduit and said adsorbent is less than the distance between the conduit inlet of said first conduit and said adsorbent.

2. An analyte pre-concentrator as claimed in claim 1, wherein the conduit inlet of said first conduit and the conduit outlet of said second conduit are each disposed in the second end of said housing.

3. An analyte pre-concentrator as claimed in claim 1, further comprising:
    a first fluid pathway in which fluid flows in through the first end of said housing, through said adsorbent, and out through the conduit inlet of said first conduit; and
    a second fluid pathway in which fluid flows in through the conduit outlet of said second conduit, through said adsorbent, and out through the first end of said housing.

4. An analyte pre-concentrator as claimed in claim 1, further comprising:
    a headspace sampler in fluid communication with said adsorbent housing for providing the sample containing the analytes thereto; and
    a chromatographic column in fluid communication with said adsorbent housing for receiving the analytes therefrom.

5. An analyte pre-concentrator as claimed in claim 4, further comprising:
    a first fluid pathway in which fluid flows from said headspace sampler, in through the first end of said housing, through said adsorbent, and out through the conduit inlet of said first conduit; and
    a second fluid pathway in which fluid flows in through the conduit outlet of said second conduit, through said adsorbent, out through the first end of said housing, and into said chromatographic column.

6. An analyte pre-concentrator as claimed in claim 1, further comprising:
    a sample vessel in fluid communication with said adsorbent housing for providing the sample containing the analytes thereto; and
    a chromatographic column in fluid communication with said adsorbent housing for receiving the analytes therefrom.

7. An analyte pre-concentrator as claimed in claim 6, further comprising:

a first fluid pathway in which fluid flows from said sample vessel, in through the first end of said housing, through said adsorbent, and out through the conduit inlet of said first conduit; and a second fluid pathway in which fluid flows in through the conduit outlet of said second conduit, through said adsorbent, out through the first end of said housing, and into said chromatographic column.

8. An analyte pre-concentrator as claimed in claim 6, wherein said sample vessel has a first end and a second end, further comprising:

a second adsorbent disposed in said sample vessel;

a third conduit in fluid communication with the second end of said sample vessel for venting fluid that has passed through said second adsorbent; and a fourth conduit in fluid communication with the second end of said sample vessel for supplying fluid to said sample vessel during desorption of the analytes from said second adsorbent;

wherein said third conduit has a conduit inlet for receiving fluid from said sample vessel, said fourth conduit has a conduit outlet for discharging fluid into said sample vessel, and the conduit inlet of said third conduit is different from the conduit outlet of said fourth conduit.

9. An analyte pre-concentrator as claimed in claim 8, further comprising: a first fluid pathway in which fluid flows in through the first end of said sample vessel, through said second adsorbent, and out through the conduit inlet of said third conduit;

a second fluid pathway in which fluid flows in through the conduit outlet of said fourth conduit, through said second adsorbent, out through the first end of said sample vessel, in through the first end of said adsorbent housing, through said adsorbent therein, and out through the conduit inlet of said first conduit; and a third fluid pathway in which fluid flows in through the conduit outlet of said second conduit, through said adsorbent in said adsorbent housing, through the first end of said housing, and into said chromatographic column.

10. An analyte pre-concentrator as claimed in claim 1, wherein said adsorbent housing is a sample vessel for collecting a sample.

11. An analyte pre-concentrator as claimed in claim 1, further comprising a heating element for controlling the temperature of said adsorbent housing.

12. An analyte pre-concentrator as claimed in claim 1, further comprising a second adsorbent disposed in said adsorbent housing, wherein:

said second adsorbent is stronger than said first adsorbent; and said second adsorbent is disposed between said first adsorbent and the conduit outlet of said second conduit.

13. An analyte pre-concentrator for pre-concentrating analytes in a sample, comprising:

an adsorbent housing having a first end for receiving the sample containing the analytes and a second end;

an adsorbent disposed in said housing for adsorbing the analytes;

a first conduit having a conduit inlet disposed in the second end of said housing for venting fluid that has passed through said adsorbent; and a second conduit having a conduit outlet disposed in the second end of said housing for supplying fluid to said housing during desorption of the analytes from said adsorbent;

wherein the conduit inlet of said first conduit is different from the conduit outlet of said second conduit.

14. An analyte pre-concentrator as claimed in claim 13, wherein the conduit inlet of said first conduit is offset from the conduit outlet of said second conduit with respect to said adsorbent.

15. An analyte pre-concentrator as claimed in claim 14, wherein the distance between the conduit outlet of said second conduit and said adsorbent is less than the distance between the conduit inlet of said first conduit and said adsorbent.

16. An analyte pre-concentrator for pre-concentrating analytes in a sample, comprising:

a sorbent tube having a first end for receiving the sample containing the analytes and a second end, said sorbent tube having an adsorbent for adsorbing the analytes;

a first conduit having a conduit inlet disposed in the second end of said sorbent tube for venting fluid that has passed through said adsorbent; and a second conduit having a conduit outlet disposed in the second end of said sorbent tube for supplying fluid to said tube during desorption of the analytes from said adsorbent;

wherein the conduit inlet of said first conduit is different from the conduit outlet of said second conduit.

17. An analyte pre-concentrator as claimed in claim 16, wherein the conduit inlet of said first conduit is offset from the conduit outlet of said second conduit with respect to said adsorbent.

18. An analyte pre-concentrator as claimed in claim 17, wherein the distance between the conduit outlet of said second conduit and said adsorbent is less than the distance between the conduit inlet of said first conduit and said adsorbent.

* * * * *